(12) United States Patent
Jackson et al.

(10) Patent No.: US 9,664,663 B2
(45) Date of Patent: May 30, 2017

(54) WATER TEST ARRANGEMENT

(71) Applicant: University of Plymouth, Plymouth, Devon (GB)

(72) Inventors: Simon Jackson, Plymouth (GB); Anas Akram Sattar, Plymouth (GB); Graham Bradley, Buckfastleigh (GB)

(73) Assignee: University of Plymouth, Plymouth, Devon (GB)

( * ) Notice: Subject to any disclaimer, the term of this patent is extended or adjusted under 35 U.S.C. 154(b) by 0 days.

(21) Appl. No.: 14/905,533

(22) PCT Filed: Jul. 11, 2014

(86) PCT No.: PCT/GB2014/052127
§ 371 (c)(1),
(2) Date: Jan. 15, 2016

(87) PCT Pub. No.: WO2015/008041
PCT Pub. Date: Jan. 22, 2015

(65) Prior Publication Data
US 2016/0153953 A1    Jun. 2, 2016

(30) Foreign Application Priority Data
Jul. 15, 2013 (GB) .................................. 1312635.4

(51) Int. Cl.
*G01N 33/18* (2006.01)
*G01N 21/78* (2006.01)
(Continued)

(52) U.S. Cl.
CPC ............ *G01N 33/1826* (2013.01); *C12Q 1/04* (2013.01); *G01N 31/22* (2013.01); *G01N 33/18* (2013.01);
(Continued)

(58) Field of Classification Search
CPC .... G01N 33/18; G01N 33/1826; G01N 33/92; G01N 21/77; G01N 21/78;
(Continued)

(56) References Cited

U.S. PATENT DOCUMENTS 5,198,339 A * 3/1993 Hansen ............ G01N 33/56916
435/7.2
5,316,911 A * 5/1994 Baek .................... G01N 33/579
435/7.1
(Continued)

FOREIGN PATENT DOCUMENTS

EP       1710584      10/2006
WO    2006007180    1/2006

OTHER PUBLICATIONS

Sattar et al. Journal of Water and Health, vol. 12.1, Mar. 1, 2014, pp. 105-112.*
(Continued)

*Primary Examiner* — Maureen Wallenhorst
(74) *Attorney, Agent, or Firm* — Andrus Intellectual Property Law, LLP

(57) ABSTRACT

A method of testing water is described which includes the steps of taking a water sample to be tested, diluting the water sample to create a test water sample, applying a reagent to the water sample, heating the test water sample for a predetermined period, and using the color of the test water sample to provide an indication of the water quality.

13 Claims, 1 Drawing Sheet

(51) Int. Cl.
*C12Q 1/04* (2006.01)
*G01N 31/22* (2006.01)

(52) U.S. Cl.
CPC ......... *G01N 21/78* (2013.01); *G01N 2400/50* (2013.01)

(58) Field of Classification Search
CPC .. G01N 2400/50; G01N 31/22; Y10T 436/25; Y10T 436/25625; C12Q 1/04
USPC .... 436/39, 71, 164, 174, 179; 422/400, 500; 435/5, 29, 34, 287.1, 288.7
See application file for complete search history.

(56) References Cited

U.S. PATENT DOCUMENTS

| | | | |
|---|---|---|---|
| 2004/0241788 A1* | 12/2004 | Wainwright | G01N 33/579 435/34 |
| 2005/0124013 A1* | 6/2005 | Bonen | G01N 1/18 435/7.32 |
| 2005/0244299 A1 | 11/2005 | Dasgupta et al. | |
| 2007/0053917 A1* | 3/2007 | Robins-Browne | A61K 35/20 424/164.1 |
| 2007/0116601 A1 | 5/2007 | Patton | |
| 2013/0078665 A1 | 3/2013 | Bodapati et al. | |
| 2014/0295477 A1* | 10/2014 | Henrie | G01N 33/579 435/23 |

OTHER PUBLICATIONS

The Environment Agency, "The Determination of Chemical Oxygen Demand in Waters and Effluents," 2007, http://www.environment-agency.gov.uk/static/documents/Research/COD-215nov.pdf.
Samantha et al., "An automated sequential injection analysis system for the determination of trace endotoxin levels in water," PDA Journal of Pharmaceutical Science and Technology, 2006, 57(1):12-24.
Search Report for GB1412377.2 dated Jan. 26, 2015.
"Pyrochrome for the detection and quantification of gram negative bacterial endotoxins (Lipopolysaccharides)", Jan. 2011, http://www.acciusa.com/pdfs/accProduct/Pyrochrome_multilang_IFUs/PyrochromeIFU)PN000856_en_r3.pdf.
International Search Report and Written Opinion for PCT/GB2014/052127 dated Aug. 28, 2014.

* cited by examiner

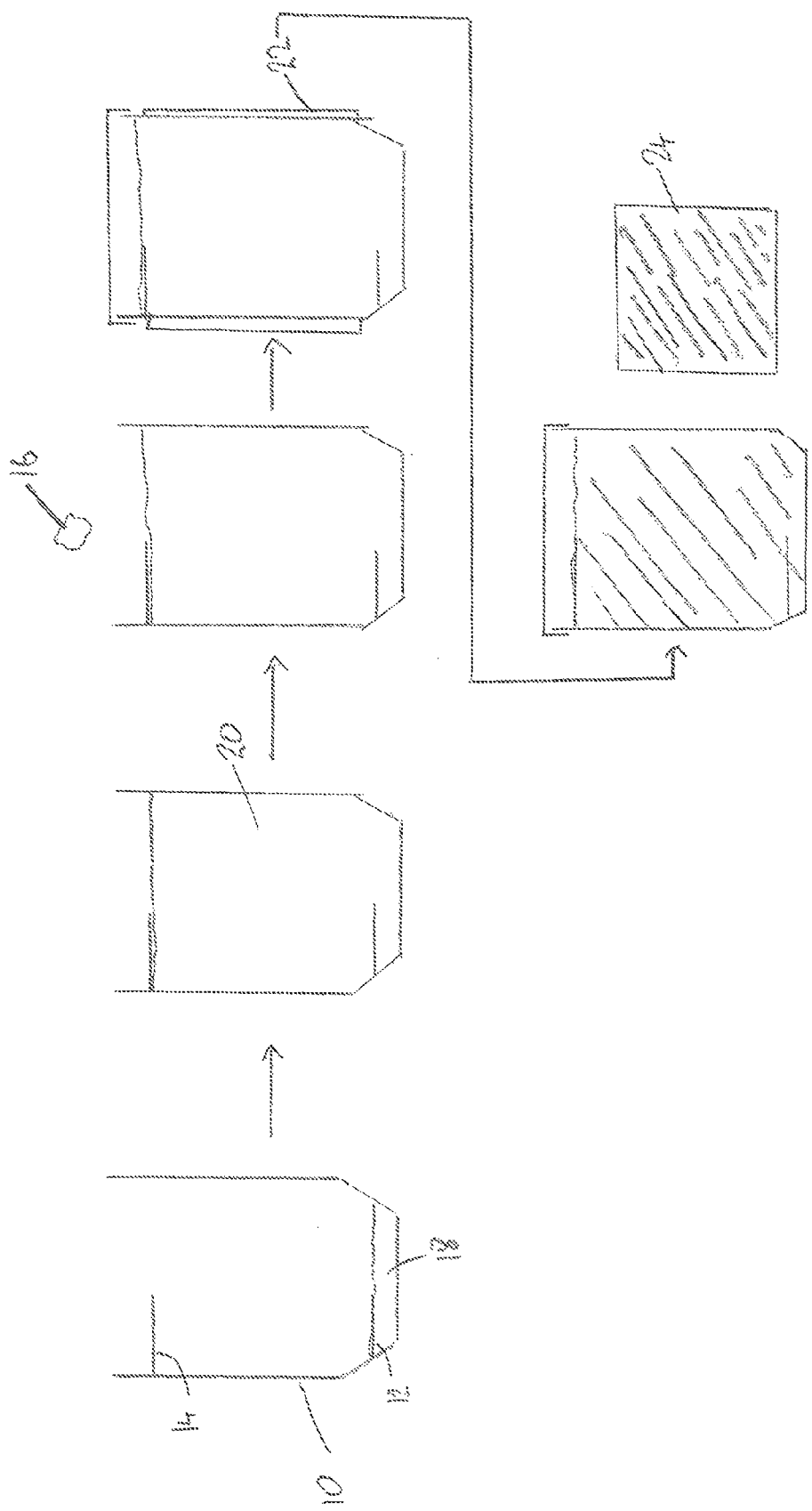

WATER TEST ARRANGEMENT

CROSS REFERENCE TO RELATED APPLICATIONS

The present application is the U.S. national stage application of International Application PCT/GB2014/052127, filed Jul. 11, 2014, which international application was published on Jan. 22, 2015, as International Publication WO2015/008041. The International Application claims priority of British Patent Application 1312635.4, filed Jul. 15, 2013, the contents of which are incorporated herein by reference in their entireties.

FIELD

This invention relates to a method and apparatus for use in testing water to provide an indication of its safety for bathing or other leisure activities, or for consumption. The test is suitable for use in the testing of either fresh water or sea water.

BACKGROUND

Water quality is periodically tested, for example to provide an indication of whether or not sea water is contaminated at beaches, and hence whether or not it is safe for bathing or undertaking other leisure activities such as surfing, body boarding, sailing, etc. The water quality tests are typically conducted by taking samples of water and undertaking testing under laboratory conditions. The tests monitor water quality by looking for the presence of faecal bacteria in the water, and usually involve producing cultures from the samples. Consequently, there is a delay of, typically, at least 24-48 hours before the test results are available. The test results are thus retrospective, providing an indication of the water quality at the time that the samples were taken, but only subsequently providing the results. Furthermore, the tests are typically only conducted on a periodic basis, and relate only to the precise location from which the sample was taken.

Given that the water quality at a given location can change rapidly, depending upon a number of factors including rainfall and other environmental conditions, such tests are of limited use in providing an indication of the current suitability of the water for undertaking various activities.

SUMMARY

It is an object of the invention to provide a method and apparatus suitable for use in testing the quality of water, the test providing a result swiftly and so providing an indication of the current condition of the water at that location.

According to the present invention there is provided a method of testing water comprising the steps of:
  taking a sample to be tested;
  diluting the sample;
  applying a reagent to the sample;
  heating the sample for a predetermined period; and
  using the colour of the sample to provide an indication of the water quality.

Preferably, the method uses the presence of bacterial lipopolysaccharide (LPS) as a marker to provide an indication of the water quality. The reagent is thus preferably sensitive to the presence of LPS.

The step of diluting the sample is preferably undertaken using endotoxin free water. The dilution of the sample serves to dilute inhibitors which may be present within the sample and which may interfere with the reaction between the LPS and the reagent. Where the sample comprises sea water, the dilution reduces the salt concentration which can inhibit the detection of LPS in the sample. Furthermore, where the reagent is very sensitive to the presence of LPS, the dilution of the sample reduces the LPS concentration within the sample to a level sufficiently low that the sample colour, after reaction with the reagent, can provide an indication of the LPS concentration within the sample. With an undiluted sample there may be insufficient variation in the sample colour, after reaction, to provide an indication of the LPS concentration.

By way of example, the dilution step conveniently dilutes to the sample to approximately 1% of its original concentration.

The reagent preferably comprises Limulus Amebocyte Lysate (LAL), and a chromogenic substrate. It may further comprise a colour developer or stabiliser and a stop reagent. The colour developer and stop reagent are preferably added to the sample after completion of the heating step.

It has been found that where the LAL and the substrate are applied together, the reagent acts considerably more slowly that where the LAL is applied to the sample and heated, and subsequently the substrate is added and heated. Where the reagent is a combination of LAL and the substrate, therefore, the heating and incubation step is preferably undertaken for a relatively long period of time, for example in the region of 18 to 19 minutes. However, the invention is not restricted in this regard and arrangements requiring or involving the use of longer or shorter incubation periods are possible within the scope of the invention.

To determine whether or not the water is safe, the colour of the sample, after reaction with the reagent, may be compared with a colour chart. The colour of the colour chart is conveniently selected to be equivalent to the colour to which a sample would turn if the test were conducted upon a sample containing the maximum safe level of LPS. If the sample turns to a colour darker than the colour chart then this provides an indication that the LPS level is above the safe level, and hence that bathing or undertaking other activities within the water is not recommended. If the sample remains lighter than the colour on the colour chart then this provides an indication that the LPS concentration is lower than the maximum safe level, and hence that the water quality is acceptable.

As an alternative, the sample colour may be compared to a control containing the maximum safe level of LPS.

The invention further relates to an apparatus for performing the method described hereinbefore. The apparatus comprises a sample tube, means for diluting a sample within the sample tube, a reagent, and means for heating the sample.

BRIEF DESCRIPTION OF THE DRAWINGS

The invention will further be described, by way of example, with reference to the accompanying drawings, in which:

The FIGURE is a diagrammatic illustration of the performance of the method of an embodiment of the invention using the apparatus according to an embodiment of the invention.

DETAILED DESCRIPTION OF THE DRAWINGS

Referring to the FIGURE, a method of testing water quality in accordance with an embodiment of the invention comprises taking a sample 18 of the water to be tested, for example by scooping the water into a test tube or vessel 10. As illustrated, the vessel 10 conveniently includes markings 12 to indicate the size sample required.

Once the sample has been taken, endotoxin free water is added to the vessel 10 to dilute the sample, forming a diluted sample 20. The quantity of water added to the vessel 10 should dilute the sample to 1% of its original concentration. If the correct volume of sample was taken, then the correct amount of water to add can be ascertained by filling the vessel 10 with endotoxin free water to a second mark 14 provided on the vessel 10.

After collection and dilution of the sample, a reagent 16 is added to the diluted sample 20. The reagent 16 provides an indication of the presence and concentration of bacterial lipopolysaccharides (LPS) within the sample. The presence of LPS can be used as a biomarker indicative of the presence of faecal bacteria within the sample. However, a background level of LPS will normally be present within a water sample, and so the manner in which the test is undertaken has to take into account the presence of the background LPS level. A test simply providing an indication that LPS is present is not sufficient. The reagent comprises a combination of Limulus Amebocyte Lysate (LAL) and a chromogenic substrate. This reagent is commercially available from GenScript Inc under the name ToxinSensor®, which is a Chromogenic LAL Endotoxin Assay Kit but is intended for use in testing for the presence of LPS in drugs, biological products, and medical devices, and so is not used in situations in which a background LPS level is expected. A similar reagent may be used in the testing of foodstuffs.

Once the reagent has been added, the sample is heated so as to incubate the sample and reagent at approximately 37° C. for 18 to 19 minutes, preferably for 18.5 minutes. One convenient way of heating the sample and reagent is to wrap the vessel 10 in a commercially available handwarmer 22. The incubation results in the LPS within the sample reacting with the LAL and producing a chromogen. If the incubation step is not performed correctly, there is a risk of inaccuracies in the test results.

Whilst reference is made herein to an incubation period in the region of 18 to 19 minutes, it will be appreciated that depending upon other parameters of the method used, longer or shorter incubation times may be more appropriate and the invention is not restricted in this regard. Indeed, the use of shorter incubation times are envisaged.

As mentioned hereinbefore, it has been found that the use of a combined reagent comprising LAL and a substrate is slower acting that where the LAL and the substrate are added separately. For example, whilst it is preferred to heat and incubate that sample and combined reagent for 18 to 19 minutes, using separate reagent components may involve heating the sample and LAL for 8 minutes, subsequently adding the substrate and heating for a further 6 minutes.

After incubation, further reagents are added to the sample. These reagents take the form of a colour developer and a stop reagent. These reagents should be added separately, as it has been found that combining them prevents the generation of accurate results. The colour developer may itself be a two (or more) component colour developer, the components of which may be mixed before use. Some colour developers are light sensitive, so preferably the colour developer is stored in an opaque or substantially opaque material container until shortly before use.

The reagents, during and after the incubation process, react with LPS within the sample, changing the colour of the sample to provide an indication of the quantity or concentration of LPS within the sample. The darker the sample colour, the greater the quantity or concentration of LPS within the sample. As the presence of LPS within the sample can be used as a marker indicative of the presence of faecal bacteria within the sample, the darker the sample colour, the greater the quantity of faecal bacteria which is present.

As mentioned hereinbefore, a background LPS level would normally be expected to be present. In addition, low levels of faecal bacteria may be acceptable. Accordingly, the test is arranged to provide an indication of whether the LPS level of the sample exceeds an acceptable level derived taking these factors into account.

In order to determine whether or not the sampled water is safe for bathing or other activities to be undertaken, the colour of the sample is compared with the colour of a printed colour chart 24. The colour of the colour chart is chosen to represent the colour to which a sample would turn if that sample contained the maximum safe level of faecal bacteria and LPS. Upon comparing the sample colour with the colour chart, if, as shown, the sample colour is lighter than the colour chart then this provides an indication that the concentration of LPS and faecal bacteria within the sample is below the maximum safe level, and hence that the water quality is acceptable for undertaking bathing or other activities. If, on the other hand, the sample colour is darker than the colour of the colour chart, then this provides an indication that the LPS, and hence faecal bacteria, content is higher than the maximum safe level and hence that the water quality is not suitable for undertaking bathing or other activities.

Whilst as described hereinbefore the sample colour is compared with the colour of a preprinted colour chart to ascertain whether or not the water quality is acceptable, it will be appreciated that as an alternative a control vessel containing a quantity of LPS equivalent to the maximum safe concentration could be tested, and the colour of the sample be compared with the colour of the control. As with the colour chart method, if the sample colour is lighter than the control then the water quality is acceptable, a sample of darker colour than the control providing an indication that the water quality is unacceptable.

It will be appreciated that the test technique described hereinbefore can be undertaken quickly and provides a substantially real time indication of the water quality. As a result, it is thought that the accuracy with which it can be determined whether or not the water quality is acceptable can be enhanced.

The step of diluting the sample prior to the addition of the reagent thereto serves to dilute the LPS within the sample to a level sufficiently low that differences in the colour of the sample, after reaction with the reagent, can be discerned, thereby giving an indication of the LPS concentration within the sample. The dilution further serves to remove or dilute any inhibitors present within the sample to a level sufficiently low that they do not interfere with the reaction between the LPS and the reagent. The reagent reaction is sufficiently strong that without dilution of the sample is may not be possible to discern whether or not the sample colour is lighter or darker than then control or chart as both would be very dark in colour. The strength of the reaction is a requisite of other applications in which the reagent is used as, in those applications, it is important to be able to demonstrate that the sample is free of LPS. No background LPS would be expected to be present in such arrangements.

It is thought that the method and apparatus may be used by bathers, surfers and other who regularly undertake water-sport activities, especially in marine locations. By testing the water in the area in which the activity is to be undertaken, factors such as the presence of rivers, streams or pipes by which liquid potentially containing bacteria flows into the sea can be taken into account. By testing the water immediately before the activity is undertaken, factors such as heavy rain which can result in increased levels of run-off water into the sea, storms causing materials which had settled onto the seabed being lifted to the surface and other factors can be taken into account.

Whilst described hereinbefore in relation to marine activities, it will be appreciated that the invention is also applicable to the testing of fresh water, such as water within lakes and rivers, prior to activities being undertaken. It could potentially also be used to provide an indication as to whether or not water is safe for consumption.

Although one embodiment of the invention is described hereinbefore, it will be appreciated that a wide range of modifications and alterations may be made thereto without departing from the scope of the invention as defined by the appended claims.

The invention claimed is:

1. A method of testing water quality comprising the steps of:
taking a water sample to be tested from a body of water at a test location at or near the body of water, the body of water taking the form of a sea, a lake or a river in which an activity is to be undertaken;
diluting the water sample at the test location to create a test water sample;
applying a reagent to the test water sample;
heating the test water sample for a predetermined period; and
using a colour of the test water sample to provide an indication of water quality at the test location,
wherein the reagent is sensitive to a presence of bacterial lipopolysaccharide (LPS) and changes colour in the event that the presence of LPS is detected, and the presence of LPS is used as a marker to provide an indication of the water quality by providing an indication of the level of faecal bacteria therein.

2. A method according to claim 1, wherein the step of diluting the water sample is undertaken using endotoxin free water.

3. A method according to claim 1, wherein the dilution step dilutes the water sample to approximately 1% of its original concentration.

4. A method according to claim 1, wherein the reagent comprises Limulus Amebocyte Lysate (LAL), and a chromogenic substrate.

5. A method according to claim 4, wherein the predetermined period is longer than would be required if the LAL and the substrate of the reagent were added and heated separately.

6. A method according to claim 5, wherein the predetermined period is approximately 18 to 19 minutes.

7. A method according to claim 4, wherein the reagent further comprises a colour developer and a stop reagent.

8. A method according to claim 7, wherein the colour developer and stop reagent are added to the test water sample, separately, after completion of the heating step.

9. A method according to claim 1, wherein the colour of the test water sample, after reaction with the reagent, is compared with a colour chart.

10. A method according to claim 9, wherein a colour of the colour chart is selected to be equivalent to a colour to which a sample would turn if the test were conducted upon a sample containing a maximum safe level of LPS.

11. A method according to claim 1, wherein the test water sample colour is compared to a control containing a maximum acceptable level of LPS.

12. A method according to claim 1, further comprising the step of undertaking an activity in or on the body of water if the indication of water quality indicates that the water quality exceeds a predetermined safe level.

13. A method according to claim 12, wherein the activity comprises at least one of swimming and surfing.

* * * * *